US007957570B2

United States Patent
Deschamps et al.

(10) Patent No.: US 7,957,570 B2
(45) Date of Patent: Jun. 7, 2011

(54) SYSTEM AND METHOD TO GENERATE AN ILLUSTRATION OF A CARDIAC REGION OF INTEREST

(75) Inventors: Thomas Deschamps, Paris (FR); Jerome F. Knoplioch, Neuilly sur Seine (FR); Laurent Launay, Saint Remy les Chevreuse (FR); Maria-Magdalena Nay, Paris (FR)

(73) Assignee: General Electric Company, Schenectady, NY (US)

( * ) Notice: Subject to any disclaimer, the term of this patent is extended or adjusted under 35 U.S.C. 154(b) by 1038 days.

(21) Appl. No.: 11/743,981

(22) Filed: May 3, 2007

(65) Prior Publication Data
US 2008/0275336 A1 Nov. 6, 2008

(51) Int. Cl.
*G06K 9/00* (2006.01)
(52) U.S. Cl. .......................................... 382/128; 600/481
(58) Field of Classification Search .................. None
See application file for complete search history.

(56) References Cited

U.S. PATENT DOCUMENTS

| | | | | |
|---|---|---|---|---|
| 6,171,241 | B1 * | 1/2001 | McVeigh et al. | 600/410 |
| 6,757,414 | B1 * | 6/2004 | Turek et al. | 382/128 |
| 7,327,872 | B2 * | 2/2008 | Vaillant et al. | 382/154 |
| 2004/0153128 | A1 * | 8/2004 | Suresh et al. | 607/14 |
| 2005/0093861 | A1 * | 5/2005 | Moreau-Gobard | 345/419 |
| 2005/0096522 | A1 * | 5/2005 | Reddy et al. | 600/407 |
| 2005/0238215 | A1 * | 10/2005 | Jolly et al. | 382/128 |
| 2007/0014452 | A1 * | 1/2007 | Suresh et al. | 382/128 |
| 2010/0027861 | A1 * | 2/2010 | Shekhar et al. | 382/131 |

OTHER PUBLICATIONS

GE Healthcare. "GE Healthcare: Cardiac fusion software application," Rt. Image, deel 20, nr. 4, Jan. 22, 2007. www.rt-image.com/ 012207TS.

Oliver Gaemperli et al. European Journal of Nuclear Medicine and Molecular Imaging, Springer, Berlin, DE, "Validation of a new cardiac image fusion software for three-dimensional intefration of myocardial perfusion SPECT and stand-alone 64-slice CT angiography," deel 34, nr. 7, Jan. 24, 2007. p. 1099, col. 2, para 2 and Fig. 1b., Issn: 1619-7089.

(Continued)

*Primary Examiner* — Bhavesh M Mehta
*Assistant Examiner* — Tahmina Ansari
(74) *Attorney, Agent, or Firm* — Fletcher Yoder P.C.

(57) ABSTRACT

A system and method to generate an illustration of a cardiac region of interest of an imaged subject is provided. The method includes generating a three-dimensional model from a series of acquired images of the cardiac region of interest; measuring a series of values of at least one functional parameter of the cardiac region of interest; generating a map of a spatial relation of the plurality of values of the functional parameter in spatial relation to the three-dimensional model of the cardiac region of interest; generating a three-dimensional model of a vessel structure leading to the cardiac region of interest; generating an output image that includes combining the three-dimensional model of the cardiac region of interest, the map of the series of values of the functional parameter, and the three-dimensional model of the vessel structure in spatial relation to one another relative to a common coordinate system.

17 Claims, 5 Drawing Sheets

OTHER PUBLICATIONS

Oliver Gaemperli et al. European Journal of Nuclear Medicine and Molecular Imagining, Springer, Berlin, DE, "Accuracy of 64-slice CT angiography for the detection of functionally relevant coronary stenoses as assessed with myocardial perfusion SPECT," deel 34, nr. 8, Jan. 12, 2007. pp. 1162-1171, Issn: 1619-7089.

GE Healthcare, "CardIQ Function Xpress User Guide 5199380-100, Revision 1," Feb. 2007. pp. 21-23.

SNM Advancing Molecular Imaging and Therapy: Press Release, "Two in One: Combined SPECT/ CT Image Showing Heart Lesions Named 2006 Image of the Year," Jun. 5, 2006. http://www.snm.org/index.cfm? PageID=5210&RPIS=627&Archive=1>.

GE Healthcare, "CardIQ Fusion PET CardIQ Fusion SPECT, User Guide 5167288-100, Revision 4," Apr. 2008.

Fratt, Lisa. "Multimodality Cardiac Diagnosis: Cardiac Fusion Imaging Comes to the Desktop." Health Imaging & IT. http://www.healthimaging.com/content/view/5872/68. Feb. 1, 2007, p. 1-3.

"User Manual for CardIQ Fusion." General Electric Company. Jan. 2007, p. 1-30.

Fahmy, Sameh, "Saving Time, Money and Lives," Somatom Sessions—Siemens Medical, (Jun. 14th-Jun. 17th, 2006), No. 18, p. 9.

Brochure of Medis medical imaging systems, Inc. entitled "QMass©CT," (2005), p. 1-2.

\* cited by examiner

US 7,957,570 B2

SYSTEM AND METHOD TO GENERATE AN ILLUSTRATION OF A CARDIAC REGION OF INTEREST

BACKGROUND OF THE INVENTION

The subject matter described herein generally relates to medical imaging, and more particularly to a system and method to generate images illustrative of a measured parameters of a region of interest (e.g., cardiac tissue of the heart) of an imaged subject.

There exists a conventional multiphase computerized tomography analysis technique to detect a potential defect in the heart (e.g., the myocardium) of a patient. A certain known representation produced by such a conventional analysis is shown as a plurality of concentric circles. Typically, all the measurements of the above-described technique are shown in a single, two-dimensional illustration of the heart muscle under analysis.

However, a drawback of the above-described representation is a difficulty to correlate the acquired measurements relative to acquired anatomical information (e.g., position of the coronary arteries) acquired in tomography datasets.

In particular, it is generally very difficult to identify or correlate a defect detected in the cardiac tissue or muscle of the heart with a problem occurring in one of the coronary arteries.

BRIEF DESCRIPTION OF THE INVENTION

The subject matter described herein is generally configured to address the drawbacks and needs described above.

In accordance with one embodiment, a method of generating an illustration of a cardiac region of interest is provided. The method includes the acts of generating a three-dimensional model from a plurality of acquired images of the cardiac region of interest; measuring a plurality of values of at least one functional parameter from one or more of the plurality of acquired images of the cardiac region of interest; generating a map of a spatial relation of the plurality of values of the at least one functional parameter in spatial relation to the three-dimensional model of the cardiac region of interest; generating a three-dimensional model of a vessel structure leading to the cardiac region of interest; and generating an output image that includes combining the three-dimensional model of the cardiac region of interest, the map of the plurality of values of the at least one functional parameter, and the three-dimensional model of the vessel structure in spatial relation to one another relative to a common coordinate system.

In accordance with another embodiment of the invention, a system to generate an illustration of a cardiac region of interest of an imaged subject is provided. The system includes an imaging system operable to generate a plurality of acquired images of the cardiac region of interest; and a controller in communication with the imaging system. The controller includes a processor operable to execute a plurality of program instructions stored in a memory. The plurality of program instructions are representative of the acts of generating a three-dimensional model from the plurality of acquired images of the cardiac region of interest, measuring a plurality of values of at least one functional parameter from one or more of the plurality of acquired images of the cardiac region of interest, generating a map of a spatial relation of the plurality of values of the at least one functional parameter in spatial relation to the three-dimensional model of the cardiac region of interest, generating a three-dimensional model of a vessel structure leading to the cardiac region of interest, and generating an output image that includes combining the three-dimensional model of the cardiac region of interest, the map of the plurality of values of the at least one functional parameter, and the three-dimensional model of the vessel structure in spatial relation to one another relative to a common coordinate system.

Embodiments of varying scope are described herein. In addition to the aspects described in this summary, further aspects will become apparent by reference to the drawings and with reference to the detailed description that follows.

DETAILED DESCRIPTION OF THE INVENTION

Figure 1:
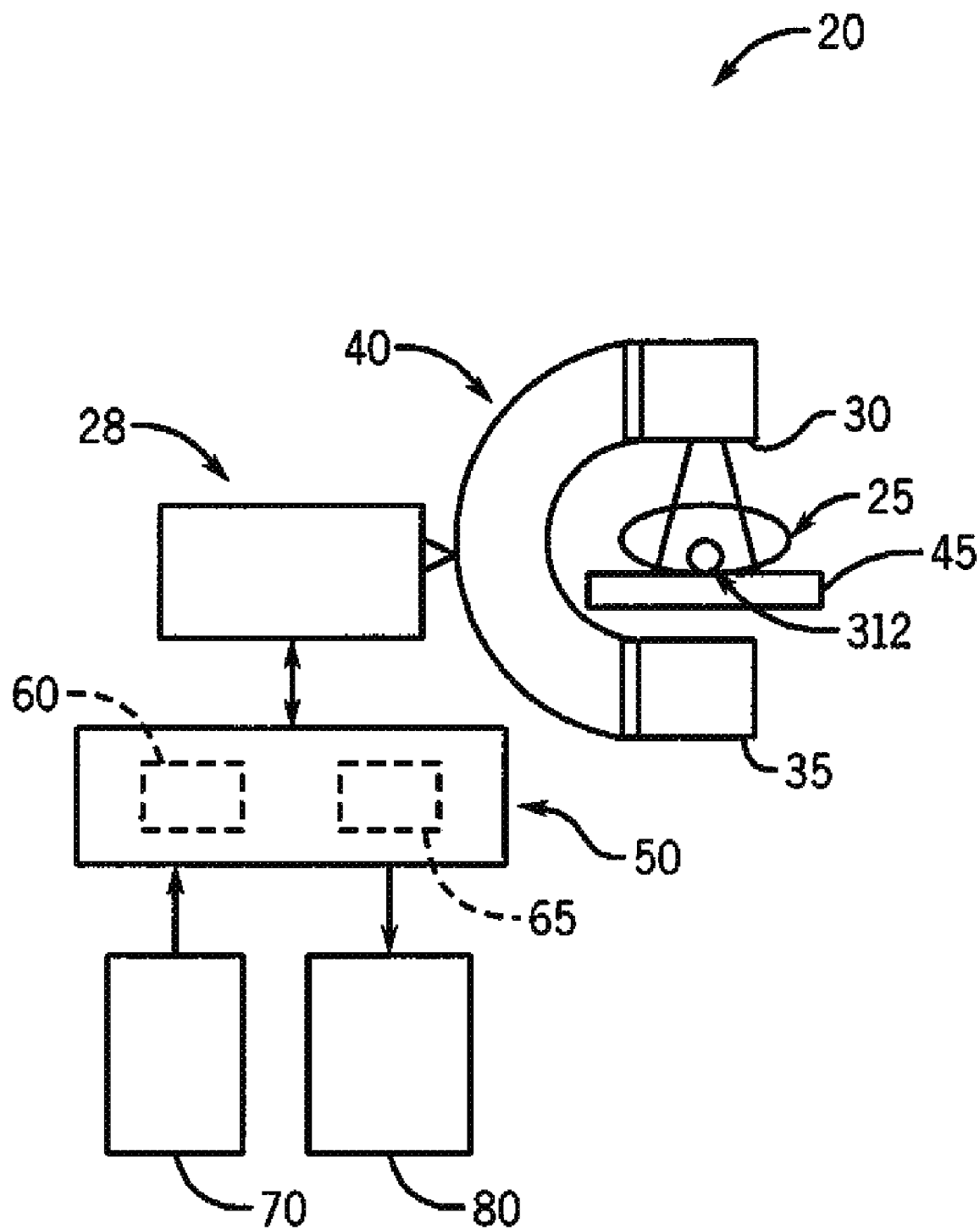
FIG. 1 is a schematic diagram of an embodiment of a system to generate a display of detected activity of a cardiac tissue of an imaged subject.

FIG. 1 shows an embodiment of a system 20 to generate a display of detected activity of a cardiac tissue of an imaged subject 25. The system 20 generally includes an imaging system 28 operable to acquire images of the imaged subject 25 from various positions. An embodiment of the imaging system 28 includes a radiation source 30 operable to emit radiation (e.g., X-rays) through an imaged subject 25 toward a detector 35. The system 20 also includes a gantry 40 in mobile support of both the source 30 and detector 35 in relation to a table 45 in support of the imaged subject 25. Yet, the type (e.g., radiological, computed tomography (CT), positron emission tomography (PET), magnetic resonance imaging (MRI), ultrasound, fluoroscopic, laparoscopic, etc.) of imaging system 28 can vary.

The system 20 also generally includes a controller 50 in communication (e.g., via direct wired links, fiber optics, wireless communications, etc.) with the source 30 and detector 35. The controller 50 may be integrated with the system 20, or may be a stand-alone component or part of another stand-alone system. The controller 50 is generally operable to control operation of the source 30 (e.g., triggering an emission of an X-ray), the gantry 40 (e.g., a mobile support of the source 30 and detector 35 relative to the imaged subject 25), and the detector 35 (e.g., synchronization of a scanning frequency of the detector 35 with the source 30, recovering image data acquired by the detector 35). An embodiment of the controller 50 generally includes a processor 60 in communication with a memory 65. The memory 65 is generally operable to receive and store computer readable program instructions for execution by the processor. The memory 65 is also generally operable to store acquired image data communicated by the detector 35 or from other sources (e.g., MRI systems, PET imaging system, picture archival system (PACS), etc.). The type of memory 65 can include disk storage, tape drive, random access memory (RAM), read-only memory (ROM), flash memory, compact disk (CD), digital versatile disks (DVDs), magnetic cassettes, magnetic tape, magnetic disk storage, or any other medium operable to be used to store computer readable instructions.

In accordance with one embodiment, the memory 65 of the controller 50 includes storage of a conventional software package generally operable to generate a three-dimensional image or model of an anatomy structure of interest in a known. Examples of the software package is INNOVA®, LIGHT-SPEED VCT™, or 5-BEAT CARDIAC™ as manufactured by GENERAL ELECTRIC®, the BRILLIANCE® CT or MX CT as manufactured by PHILLIPS®, the SOMATOM® CT as manufactured by SIEMENS®. The system 20 in combination with the software package is generally operable to generate a three-dimensional reconstructed image of an anatomical structure of the imaged subject 25 from a series of acquired image frames representative of image data acquired as slices of the anatomical structure of the imaged subject 25.

The controller 50 is also in communication with an input or input device 70 and an output or output device 80. Examples of the input 70 include a keyboard, joystick, mouse device, touch-screen, pedal assemblies, track ball, light wand, voice control, or similar known input device. Examples of the output 80 include a monitor, a touch-screen, a printer, light-emitting diodes, audible devices, a pager, a cell phone, a personal data assistant (PDA), etc.

Figure 2:
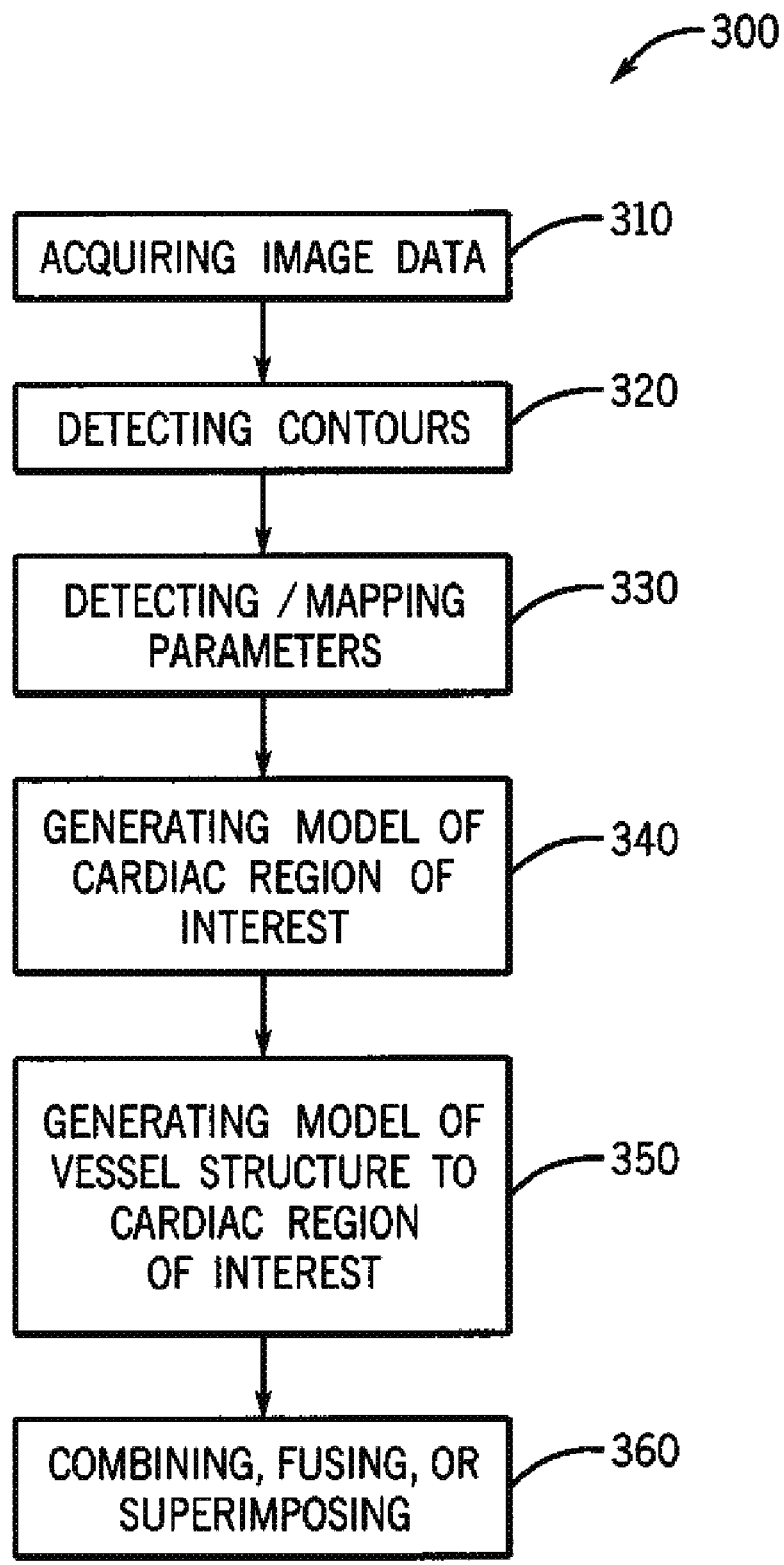
FIG. 2 is a schematic diagram representing an embodiment of a method of displaying activity of a cardiac tissue of an imaged subject.

Having described the general construction of the system 20, the following is general description of a method 300 of operating the system 20 in generating a display illustrative of the physiological activity of an anatomical structure of interest in the imaged subject 25. FIG. 2 illustrates an embodiment of the method 300. A technical effect of the system 20 and method 300 is to convert a sequence of acquired two-dimensional images of the cardiac tissue of the patient into a display illustrative of a map of measured values of functional parameters of an anatomical structure of interest of the imaged subject 25. It should be understood that the foregoing sequence of acts or steps comprising the method 300 can vary, that the method 300 does not need to include each every act described herein, and the method 300 can include additional acts not described herein. It should also be understood that one or more of the following acts of the method 300 can be represented as a computer-readable program instruction stored in the memory 65 for execution by the controller 50.

Figure 3:
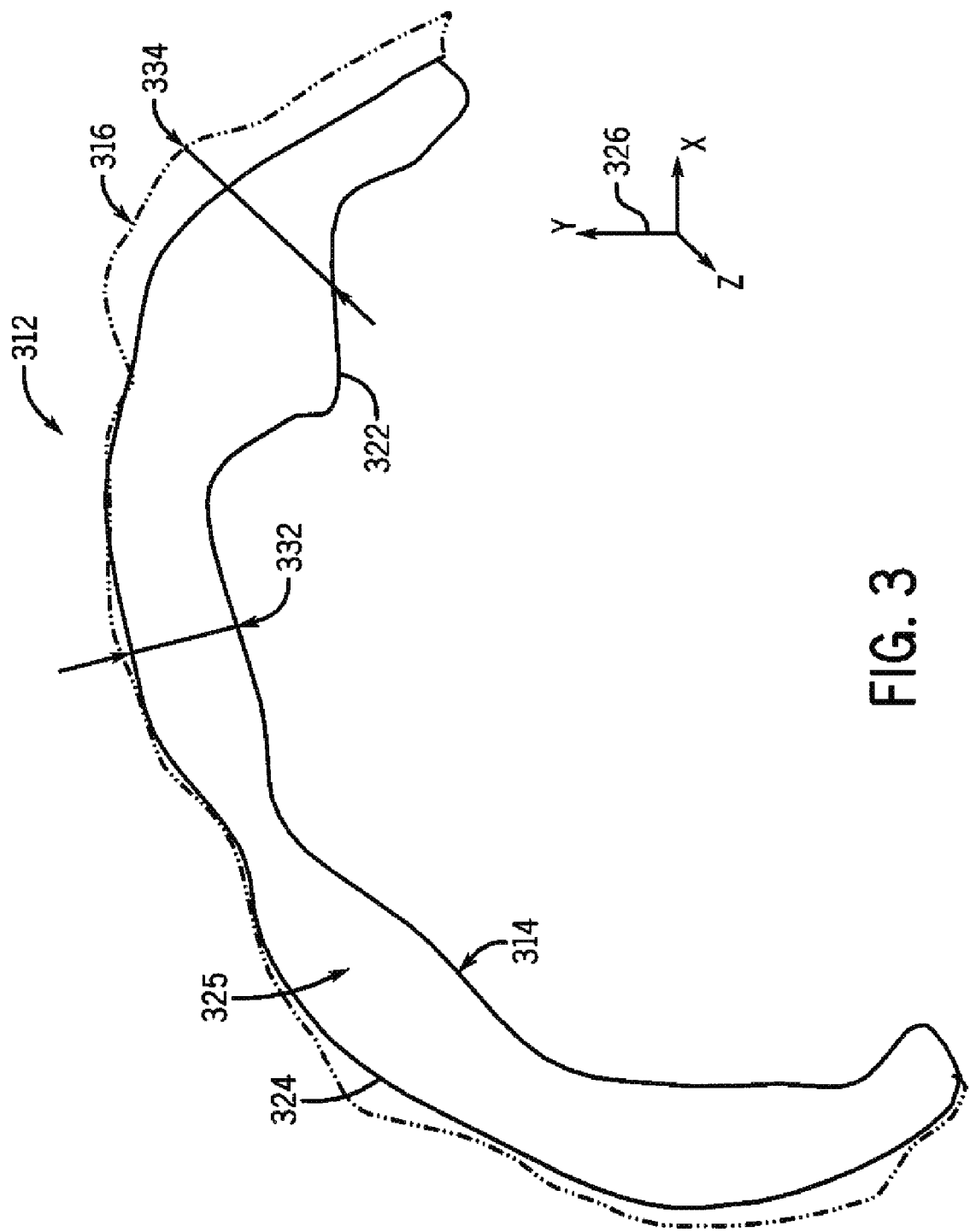
FIG. 3 is a schematic diagram illustrative of an embodiment of an image or model of a cardiac region of interest of the imaged subject.

Referring to FIG. 2, act 310 includes acquiring image data (e.g., radiological, computed tomography (CT), magnetic resonance imaging (MRI), laparoscopic, fluoroscopic, positron emission tomosynthesis (PET), ultrasound, etc.) of a region of interest 312 of the imaged subject 25 (See FIG. 1). Referring to FIG. 3, a particular example of the acquired image data includes a first image (illustrated in solid line and by reference 314) of the cardiac tissue or region of interest in a systole phase (i.e., contraction phase), and a second image (illustrated by dashed line and reference 316) of the cardiac tissue or region of interest in a diastole phase (i.e., expansion phase). The acquired image data is communicated for storage in the memory 65 of the controller 50.

Act 320 includes detecting or identifying illustrations of contours or anatomical structure of the region of interest 312 (e.g., cardiac tissue) in the acquired image data. According to the particular example as illustrated in FIG. 3, act 320 includes identifying an inner wall or endocardium contour 322 and an outer wall or epicardium contour 324 that defines limits of the region of interest 312 of heart muscle or myocardium 325 therebetween. According to one embodiment, act 320 includes registering the locations of the contour or anatomical structure 322 and 324 in spatial relation relative a coordinate system 326.

Referring back to FIG. 2, act 330 includes detecting and/or mapping values of one or more functional parameters of the region of interest 312 of the imaged subject 25 (See FIG. 1) in spatial relation to the contours 322 and 324 and/or coordinate system 326 (See FIG. 3). In accordance with the particular example, act 330 includes detecting or measuring values of selected functional parameters from acquired image data of a series of positions of the region of interest 312 of cardiac tissue of the imaged subject 25. A technical effect of detecting values of one or more functional parameters of the cardiac region of interest 312 allows detection of defects that affect the heart of the imaged subject 25.

Referring to FIG. 3, an example of act 330 (See FIG. 2) includes measuring a thickness or distance 332 of cardiac tissue between the endocardium and epicardium contours 322 and 324. Another example of a measured functional parameter includes an amplitude of motion 334 of the myocardium 325. An example of measuring the amplitude of motion 334 includes detecting a distance between the contour of the endocardium 322 at the systole phase (314) of the cardiac tissue relative to the contour of the epicardium 322 at the dystole phase (316) of the cardiac tissue. The controller 50 is also operable to detect or identify and calculate a location of the amplitude of motion 334 of the myocardium 325 relative to the common coordinate system 326 and/or landmarks 322 or 324 of the anatomical structure of the region of interest 312.

Yet another example of a measured functional parameter in act 330 includes a density of the myocardium cardiac tissue 325 between the endocardium and the epicardium contours 322 and 324. In measuring density of the cardiac tissue, the controller 50 measures or calculates values for selected parameters (e.g., greyscale values) of each pixel or group of pixels as acquired in the image data of the region of interest 312 of the imaged subject 25. Using conventional imaging processing techniques, the controller 50 is operable to translate this detected greyscale information to calculate (e.g., via a predetermined lookup table) a variation in density of the myocardium 325 relative to a location between the endocardium contour 322 and the epicardium contour 324.

Figure 4:
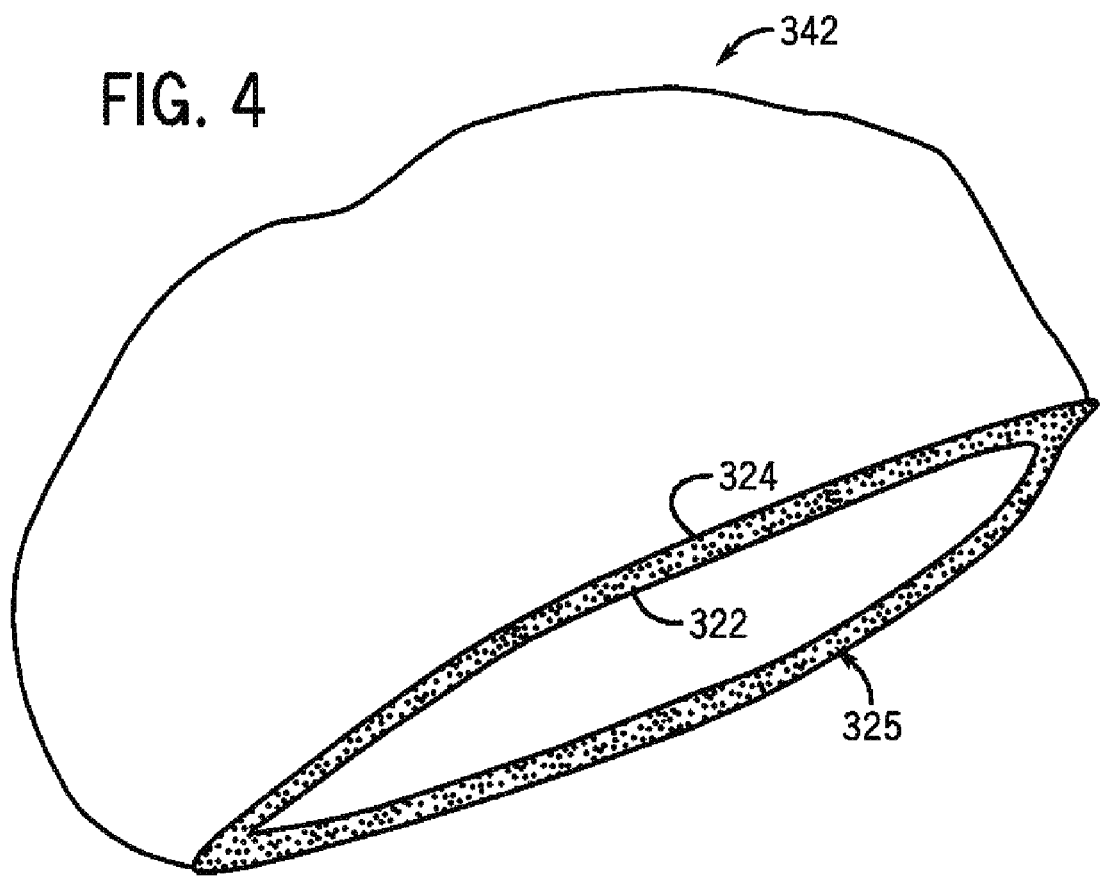
FIG. 4 is a schematic diagram illustrative of an embodiment of a second three-dimensional reconstructed model generated by the system of FIG. 1, the second three-dimensional reconstructed model representative of a cardiac tissue or heart muscle in the region of interest of the imaged subject.

Act 340 includes generating a three-dimensional model of the region of interest 312. Referring to FIG. 4, an embodiment of act 340 (See FIG. 2) includes applying the ray tracing technique (e.g., between the endocardium contour 322 and the epicardium contour 324) so as to generate a three-dimensional reconstructed model or illustration 342 of the cardiac tissue alone in the region of interest 312.

Figure 5:
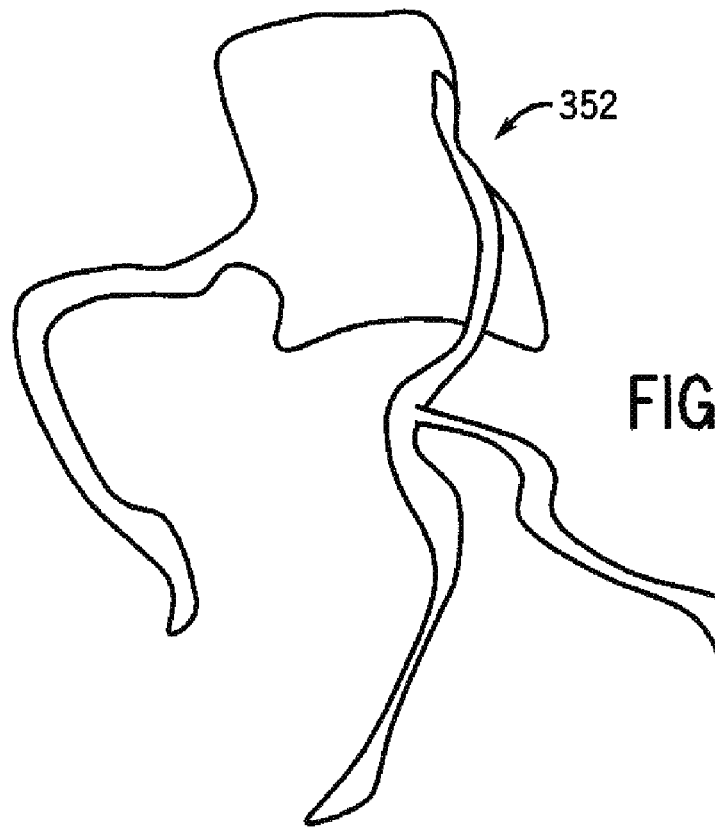
FIG. 5 is a schematic diagram showing an embodiment of a first three-dimensional reconstructed model generated by the system of FIG. 1, the first three-dimensional reconstructed model representative of a vessel structure of the imaged subject.

Referring now to FIG. 5, act 350 (See FIG. 2) includes generating a three-dimensional model 352 representing a blood vessel structure 352 (e.g., coronary tree) alone, individually, and separately that leads to the cardiac tissue represented by three-dimensional model 342 created in act 340 and shown in FIG. 4. An embodiment of the act 350 includes applying a segmentation technique to the acquired image data in a conventional manner so as to detect the blood vessel structure 352 (e.g., coronary artery tree) leading to the cardiac region of interest 312.

Figure 6:
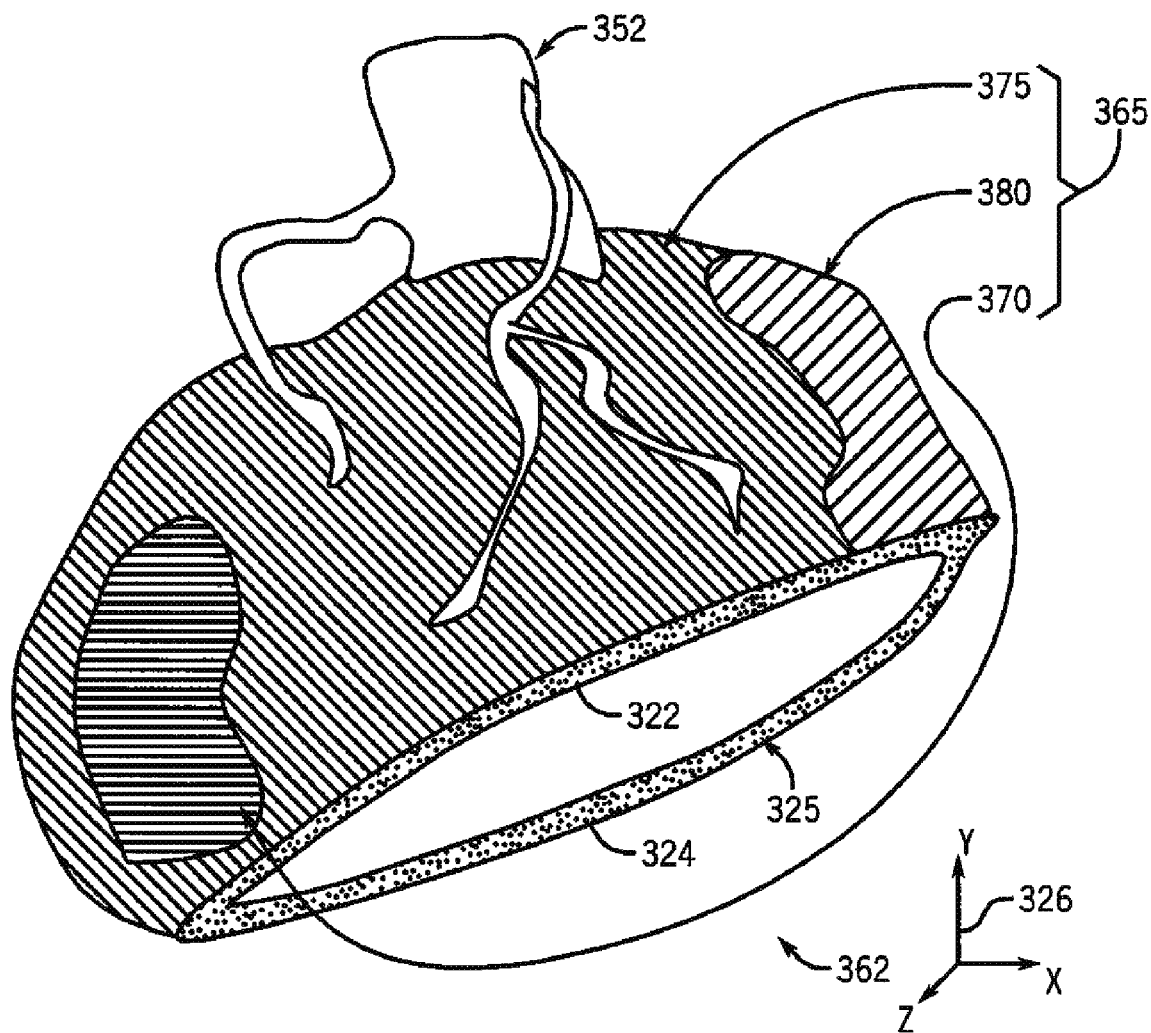
FIG. 6 is a schematic diagram illustrative of an embodiment of an output image including the first three-dimensional reconstructed model of FIG. 3 that is fused, combined, or superimposed with the second three-dimensional reconstructed model of FIG. 4 in combination with a map of values of a selection functional parameter of the region of interest.

As illustrated in FIG. 6, act 360 (See FIG. 2) includes combining, fusing, or superimposing, the three-dimensional reconstructed model 342 (See FIG. 4) of the cardiac tissue of interest generated in step 340 with the three-dimensional reconstructed model 352 (See FIG. 5) of the blood vessel structure 352 generated in act 350 so as to create or generate an output image 362 (See FIG. 5) including the model of the cardiac tissue 342 in spatial relation to model the blood vessel structure 352 relative to the common coordinate system 326 for illustration at the output 80.

Referring to FIG. 6, the combined three-dimensional model 362 can further include an a map or illustration 365 of selected locations of measured values of one or more functional parameters detected or calculated in act 330. Using the ray tracing technique noted above, an embodiment of the map 365 of measured values of the functional parameters relative to location (e.g., via a look-up table) is illustrated in superimposition over the three-dimensional model 342 of the cardiac tissue alone, or otherwise the output image 362. The map 365 of values of the functional parameters can include different bands or spectrums of color (e.g., blue as illustrated by horizontal lines and reference 370, green as illustrated by diagonal lines and reference 375, orange as represented by cross-hatching lines and reference 380) representative of a predetermined range of detected values of the functional parameter in spatial relation to the three-dimensional model of the cardiac region of interest. Of course, it should be understood that the selected spectrum or band of color can vary. Although the subject matter is described with respect to illustration with different bands or spectrums 370, 375, and 380 of color, it should be understood that the map 365 can include alternative types of illustrations (e.g., numerical, alphabetical, greyscale, etc.) to represent the values of functional parameters of the cardiac tissue.

A technical effect of the system 20 and method 300 is to generate the output image 362 that simultaneously shows or visualizes detected values of the functional parameters in spatial relation with the anatomy of the cardiac tissue 342 or heart muscle relative to the blood vessel structure 352 leading to the cardiac tissue. Another technical effect of the system 20 and method 300 is to generate an intuitive presentation of functional information (density, thickness, motion) relative to morphological information (position of the coronary artery tree 352 relative to a defect identified by the map 365) to aid in detecting a functional defect in the heart muscle (shown by a variation of coloration of the heart muscle) and to correlate the detected functional defect with the corresponding blood vessel structure 352. Although the above description is in reference to a cardiac region of interest, it should be understood that the system 20 and method 300 is applicable to other regions (e.g., brain, liver, lungs, etc.) of the imaged subject 25.

This written description uses examples to disclose the subject matter, including the best mode, and also to enable any person skilled in the art to make and use the subject matter described herein. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A method of generating an illustration of a cardiac region of interest of an imaged subject, the method comprising acts of:
   generating a three-dimensional model of cardiac tissue from a plurality of acquired images of the cardiac region of interest;
   measuring a plurality of values of at least one functional parameter from one or more of the plurality of acquired images of the cardiac region of interest;
   generating a map of a spatial relation of the plurality of values of the at least one functional parameter in spatial relation to the three-dimensional model of the cardiac tissue;
   generating a three-dimensional model of a blood vessel structure leading to the cardiac tissue, wherein the act of generating the three-dimensional model of the blood vessel structure includes identifying the blood vessel structure in one or more of the plurality of acquired images, and the three-dimensional model of the blood vessel structure is independent of the three-dimensional model of the cardiac tissue; and
   generating an output image that includes combining the three-dimensional model of the cardiac tissue, the map of the plurality of values of the at least one functional parameter, and the three-dimensional model of the blood vessel structure in spatial relation to one another relative to a common coordinate system.

2. The method according to claim 1, the method further comprising the acts of:
   identifying an endocardium contour or an epicardium contour delimiting a myocardium of the cardiac tissue, and
   calculating a value of at least one functional parameter of the myocardium.

3. The method according to claim 2, wherein the at least one functional parameter comprises a thickness of the myocardium, said parameter being calculated as a distance between the endocardium contour and the epicardium contour.

4. The method according to claim 2, wherein the at least one functional parameter comprises a motion amplitude of the myocardium, wherein measuring the motion amplitude includes detecting a distance between an endocardium contour isolated in a first of the plurality of images acquired during a systole phase of the cardiac region of interest and an endocardium contour isolated in a second of the plurality of images acquired during a diastole phase of the cardiac tissue.

5. The method according to claim 4, wherein the at least one functional parameter comprises a density of the myocardium, wherein measuring the density of the myocardium includes detecting grayscale value of pixels between the endocardium contour and the epicardium contour as illustrated in one or more of the plurality of acquired images of the cardiac region of interest.

6. The method according to claim 1, wherein the act of generating the three-dimensional model of the cardiac tissue includes applying a ray tracing technique to the plurality of acquired images so as to generate a three-dimensional volume rendering view of the cardiac tissue.

7. The method according to claim 1, wherein the three-dimensional model of the blood vessel structure includes a view of the coronary arteries leading to the cardiac tissue.

8. The method according to claim 1, wherein the plurality of acquired images are generated using a computed tomography imaging system.

9. A system to generate an illustration of a cardiac region of interest of an imaged subject, comprising:

an imaging system operable to generate a plurality of acquired images of the cardiac region of interest; and a controller in communication with the imaging system, the controller including a processor operable to execute a plurality of program instructions stored in a memory, the plurality of program instructions representative of the acts of:

generating a three-dimensional model of cardiac tissue from the plurality of acquired images of the cardiac region of interest, measuring a plurality of values of at least one functional parameter from one or more of the plurality of acquired images of the cardiac region of interest, generating a map of a spatial relation of the plurality of values of the at least one functional parameter in spatial relation to the three-dimensional model of the cardiac tissue, generating a three-dimensional model of a blood vessel structure leading to the cardiac tissue, wherein the act of generating the three-dimensional model of the blood vessel structure includes identifying the blood vessel structure in one or more of the plurality of acquired images, and the three-dimensional model of the blood vessel structure is independent of the three-dimensional model of the cardiac tissue, and generating an output image that includes combining the three-dimensional model of the cardiac tissue, the map of the plurality of values of the at least one functional parameter, and the three-dimensional model of the blood vessel structure in spatial relation to one another relative to a common coordinate system.

10. The system according to claim 9, further including program instructions representative of the acts of:

identifying an endocardium contour or an epicardium contour delimiting a myocardium of the cardiac tissue, and calculating a value of at least one functional parameter of the myocardium.

11. The system according to claim 10, wherein the at least one functional parameter comprises a thickness of the myocardium, said parameter being calculated as a distance between the endocardium contour and the epicardium contour.

12. The system according to claim 10, wherein the at least one functional parameter comprises a motion amplitude of the myocardium, wherein measuring the motion amplitude includes detecting a distance between an endocardium contour isolated in a first of the plurality of images acquired during a systole phase of the cardiac region of interest and an endocardium contour isolated in a second of the plurality of images acquired during a diastole phase of the cardiac tissue.

13. The system according to claim 10, wherein the at least one functional parameter comprises a density of the myocardium, wherein measuring the density of the myocardium includes detecting grayscale value of pixels between the endocardium contour and the epicardium contour as illustrated in one or more of the plurality of acquired images of the cardiac region of interest.

14. The system according to claim 9, wherein the act of generating the three-dimensional model of the cardiac tissue includes applying a ray tracing technique to the plurality of acquired images so as to generate a three-dimensional volume rendering view of the cardiac tissue.

15. The system according to claim 9, wherein the three-dimensional model of the blood vessel structure includes a view of the coronary arteries leading to the cardiac tissue.

16. The system according to claim 9, wherein the imaging system includes a computed tomography imaging system.

17. The system according to claim 9, the map including different bands of color representative of a given range values of the functional parameter in spatial relation to the three-dimensional model of the cardiac tissue.

* * * * *